Figures 1, 3:
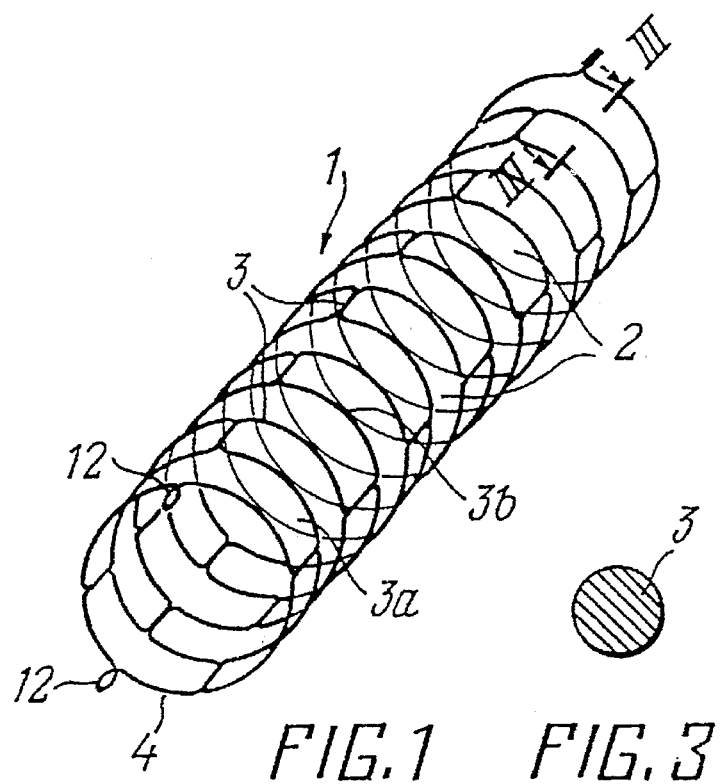

United States Patent [19]

Kavteladze et al.

[11] Patent Number: 5,643,339
[45] Date of Patent: Jul. 1, 1997

[54] PROSTHETIC DEVICE FOR SUSTAINING A BLOOD-VESSEL OR HOLLOW ORGAN LUMEN

[75] Inventors: Zaza A. Kavteladze; Aleksandr P. Korshok; Andrej A. Kadnikov, all of Moscow, Russian Federation

[73] Assignee: William Cook Europe A/S, Denmark

[21] Appl. No.: 379,582

[22] PCT Filed: Aug. 6, 1993

[86] PCT No.: PCT/DK93/00256

§ 371 Date: Feb. 1, 1995

§ 102(e) Date: Feb. 1, 1995

[87] PCT Pub. No.: WO94/03127

PCT Pub. Date: Feb. 17, 1994

[30] Foreign Application Priority Data

Aug. 6, 1992 [RU] Russian Federation ......... 5057852

[51] Int. Cl.$^6$ ............................................. A61F 2/06
[52] U.S. Cl. .............................. 623/1; 606/194; 623/12
[58] Field of Search ........................ 623/1, 12; 606/192, 606/194, 195, 108

[56] References Cited

U.S. PATENT DOCUMENTS

| 4,503,569 | 3/1985 | Dotter . | |
|---|---|---|---|
| 5,037,427 | 8/1991 | Harada et al. | 623/1 |
| 5,102,417 | 4/1992 | Palmaz | 606/195 |
| 5,135,536 | 8/1992 | Hillstead . | |
| 5,234,457 | 8/1993 | Andersen | 623/1 |
| 5,354,308 | 10/1994 | Simon et al. | 623/1 |
| 5,360,443 | 11/1994 | Barone et al. | 623/1 |
| 5,366,472 | 11/1994 | Hillstead | 606/192 |
| 5,370,683 | 12/1994 | Fontaine | 623/1 |
| 5,397,359 | 3/1995 | Mittelmeier et al. | 623/1 |
| 5,405,377 | 4/1995 | Cragg | 623/1 |

FOREIGN PATENT DOCUMENTS

| 0221570 | 5/1987 | European Pat. Off. . |
| 0464755 | 1/1992 | European Pat. Off. . |
| 3918736 | 12/1990 | Germany . |
| 1237201 | 8/1993 | U.S.S.R. . |

OTHER PUBLICATIONS

Rosch, J., et al., "Modified Gianturco Expandable Wire Stents in Experimental and Clinical Use," *Ann. Radiol.*, 1988, vol. 31, No. 2, pp. 100–103.

Primary Examiner—John G. Weiss
Assistant Examiner—Bruce E. Snow
Attorney, Agent, or Firm—Richard J. Godlewski

[57] ABSTRACT

A prosthetic device for sustaining a vessel or hollow organ lumen (a stent) has a tubular wire frame (1) with rows of elongate cells (2) having a larger axis and a smaller axis. The cells are arranged with the larger axis in the circumferential direction of the frame (2) and the smaller axis parallel to the axial direction thereof. Each cell is formed by two U-shaped wire sections, and in a plane perpendicular to the longitudinal axis one of the branches of the U-shaped wire sections in one row form together a closed ring-shape (4) which provides the frame (1) with large radial stiffness. In the axial direction the frame (1) has only low stiffness so that it easily conforms to the vascular wall even if this deforms due to external loads. The interconnection between the cells (2) may be flexible.

20 Claims, 4 Drawing Sheets

PROSTHETIC DEVICE FOR SUSTAINING A BLOOD-VESSEL OR HOLLOW ORGAN LUMEN

The invention pertains to the field of medical equipment, and to be more exact to a prosthetic device for sustaining a vessel or hollow organ lumen, having a wire frame in form of a flexible tubular shaped body which in development is formed by many rows of interconnected cells, each of which cells comprises two U-shaped wire sections formming together approximately an elongated oval with a larger axis and a smaller axis, wherein adjacent cells in neighbouring rows are shifted by half of the larger axis of the oval with respect to each other in the direction of the larger axis and are shifted by the smaller axis of the oval with respect to each other in the direction of the smaller axis.

Various diseases of blood-vessels or hollow organs cause a stenosis or complete obturation (occlusion) of their lumen, which results in a decrease or complete loss of their functional attributes.

The wide spread of diseases of this kind demands an elaboration of quite new methods of medical treatment.

The device for sustaining of the blood-vessel or hollow organ lumen has a tubular shaped frame body, which is introduced in the vessel or hollow organ, fixed in the necessary place and sustains its lumen.

The problem of designing such devices has already a twenty year history.

Nevertheless, a universal reliable device satisfying all necessary requirements has as yet not been created.

The device for sustaining of the vessel or hollow organ lumen should satisfy the following requirements:

effectively fulfil the function of recovery and sustaining of the vessel or hollow organ lumen;

have a reliable and simple in control delivery system;

possibility of use within a wide range of sizes from 3 to 50 mm and more;

have biological compatibility with the organism tissues;

posibility of use in different anatomical areas of vessels and hollow organs;

minimum traumatism during and after operation;

stiffness of the construction to provide counteraction to in situ external compression forces.

An attempt to create a device compatible with the organism tissues was undertaken in the USSR patent No. 1237201, dated Feb. 15, 1986.

This known device for sustaining the vessel or hollow organ lumen represents a wire frame having a tubular shaped body. The frame is formed by a wire element, having round or square cross-section and arranged in a cylindrical helical line. The frame has a shape of a helical cylindrical spring and it is furnished with fixing elements to keep it on the device for delivery into the vessel or hollow organ. Each fixing element is made in form of a loop, one of which is formed at the initial section of the wire element, and the other at its final section. The facility for delivery of the above device to the vessel or hollow organ comprises an introducer in form of a X-ray contrast tube and another X-ray contrast tube of a lesser diameter, on whose surface the device is secured by means of a connecting element. The material of the frame wire is an alloy of the titanium-nickel system, which is biologically compatible with the organism tissues.

The device known from the USSR patent is reliable in use. However, it is expedient to use the known device in vessels or hollow organs having a diameter of not more than 8 mm, which is conditioned by the value of the ultimate strain of the frame material limited by 8% (the so-called strain limit of the shape memory effect), as well as by the demand of minimizing the puncture hole (hole in vessel through which the device is introduced into the organism). The device may only to a limited extent withstand external compression forces.

The use of the known device in vessels and hollow organs with a diameter exceeding 8 mm, and at preservation of the condition of not exceeding the ultimate strain of the frame material, would demand a decrease of the thickness of the wire frame elements, which would result in a further loss of stiffness of the frame, or in a necessity to increase the diameter of the puncture hole, which in turn would cause an intolerable traumatism of the vascular or hollow organ walls.

Thus, the mentioned construction of the device for sustaining the vessel or hollow organ lumen is applicable only for vessels or hollow organs, whose diameter is less than 8 mm which sharply narrows the field of its application.

The execution of the function of effective recovery and sustaining of the vessel or hollow organ lumen by the described device demand an arrangement of the coils of the wire frame with a minimum lead to prevent germination of atherosclerotic patches, or counteract the occlusion. However, the making of the frame with the minumum lead between coils results in a loss of its stiffness in the vessel or hollow organ, which, under the effect of external compression forces, either results in a change of its arrangement in the vessel, i.e. the frame longitudinal axis gets arranged at an angle to the vessel axis, or in an increase of the lead between coils. Both in the first and second cases the frame stops fulfilling its main functional attribute, as a result of which the vessel or hollow organ lumen gets reduced.

As it was described above, the frame is furnished with fixing elements on the front and rear ends. The fixing elements are made in the form of loops lying in the plane perpendicular to the frame axis in such a manner that the partial overlapping of the frame lumen occurs, which causes formation of turbulent flows in the blood current and facilitates the appearance of various complications in the form, for example, of intensification of atherosclerotic formations.

The described facility of frame delivery is reliable enough in the process of introduction of the frame to the affected area. However, at installation of the frame with the aid of this facility one of the fixing loops gets released. The frame, being scragged up until this moment, gets released and uncoils in the direction opposite to the direction of coiling at its fixing, acquiring its initial shape. In the process of uncoiling, which is uncontrolled, traumatization of the vascular or hollow organ walls may occur, which has an unfavourable affect on the result of operation. In addition it should be mentioned that the frame can occupy an arbitrary position in the vessel that is uncontrolled by the surgeon.

The described frame has the shape of a helical cylindrical spring. If we examine the frame section in a plane perpendicular to the frame axis and passing through the coil surface, it is seen that the frame coil located in the plane has a break, which decreases the frame stiffness under the effect of radially acting forces.

Another device for sustaining a vessel or hollow organ lumen is known (Ann Radiol, 1988, 31, n.2, 100–103), and it has a tubular shaped wire frame formed by a wire element, which in development represents a saw-tooth line. In order to permit a change in the stiffness of the frame, the latter is bound at the tops by a caprone thread.

The branches of the wire element are arranged along the longitudinal axis of the tubular frame, which provides for a constancy of the frame linear dimensions at the delivery and installation of the frame in the affected place of the vessel or hollow organ. To fix the frame in the vascular or hollow organ walls, provision is made for fixing elements in the form of hooks.

In the described construction use is made of materials, whose ultimate elastic strain makes up tenths of a percent.

The delivery system represents an X-ray contrast tube accommodating a pusher, which is a piston with a rod. For transportation (delivery) the device is placed in the X-ray contrast tube, and by means of the rod the surgeon acts upon the piston interacting with the device.

The described device has found a wide application for sustaining the lumen of the affected areas of veins, in which there are no atherosclorotic processes. The use of this device in arterial vessels is hardly possible because of the large distances between the wire elements, which may result in germination of aterosclerotic patches and, as a consequence, in an uneffective use of this device.

The latter known device is used for sustaining the lumen of the affected areas of veins, whose diameter is within 15 to 30 mm. In this case a wire of a large diameter is used to impart the necessary stiffness to the construction. If this device were to be used in smaller vessels or hollow organs having a diameter from 3 to 15 mm it would be necessary to decrease the wire thickness (diameter). However, in this case the construction loses its thickness and may hardly provide an effective sustaining of lumen.

Due to the arrangement of the wire branches in the pheriferal direction of the tubular frame body, the given construction is stable and has a high stiffness in the axial direction, which prevents full adjustion to the vessel geometry and may traumatize the vascular or hollow organ walls.

When it is necessary to deliver the above device to the affected area along a curved path, the elastic deformation of the frame wire elements changes into a plastic deformation, which results in an irreversible change of the device shape.

Thus, delivery of the given frame to the affected place is possible only along a path close to a straight line, which considerably narrows the number of the anatomical areas, where the frame could be used.

A device of the initially mentioned kind is known from EP-A-221570. In this device the larger axis of each cell is arranged in the axial direction of the tubular body and the smaller axis in the circumferential direction thereof and the wire sections forming the cells are rigidly interconnected.

The delivery facility of the described device comprises an X-ray contrast tube with an inflatable balloon, on the outside of which the wire frame is located. To press the wire frame onto the X-ray conrast tube, provision is made for one more tube enveloping the frame on its external surface. In delivery of the frame to the affected area of the vessel or hollow organ first the external tube is removed, and the balloon is inflated so that the frame is expanded and acquires its final shape whereafter it interacts with the vascular walls. After that the X-ray contrast tube is removed from the vessel, and the frame is installed in the affected area.

Its delivery and installation in the affected area is sufficient reliable and convenient. However, the use of a rigid Joint by fusing together, soldering or welding of the wire elements in the points of their intersection seems to be unreliable because of:

a probable proceeding of electrochemical processes in the soldering zone, which may cause a damage to the joint, loss of stiffness in the frame and consequently, of the functional attributes;

formation of the so-called welding zone with a embrittled material structure, which may make this Joint unreliable.

The described device can be used for sustaining the lumen of vessels or hollow organs within a range of sizes from 3 to 8 mm. In the described construction use is made of matrials whose ultimate elastic strain makes up tenths of a percent. When it is necessary to deliver the device to the affected area along a curved path, a danger arises to exeed the ultimate elastic strain and, consequently, the proceeding of the process of plastic deformation of the frame material. Thus, the delivery of the given frame is possible only along a path close to a straight line, which essentially decreases the possibility of its use in different anatomic areas. The known device has a large stiffness in the axial direction which may traumatize the walls of the vascular or hollow organ in the regions around the ends of the device if the device supports a vascular or hollow organ which change its shape during adaption to varying external loads. Further, it is a common disadvantage of the known devices that they only to a limited extent posess a radial stiffness allowing them to support vascular or hollow organs which are not surrounded by a bone structure taking up external loads.

The invention is based on the problem of creation of a device for sustaining the vessel or hollow organ lumen, in which the shape and arrangement of cells forming the tubular frame provide the frame with a large stiffness in the radial direction and only low stiffness in the axial direction so that the device without risk of traumatization will keep the vascular or hollow organ open even if the latter changes shape due to external loads.

This is obtained by the initially mentioned device which, according to the invention, is characterized in that the larger axis of the oval is directed in the circumferential direction of the tubular body and the smaller axis parallel to the axial direction thereof so that in a plane perpendicular to the longitudinal axis of the body one of the branches of the U-shaped wire sections in one row forms together a closed ringshape.

By arranging the cells so that the larger axis of the oval is directed in the circumferential direction the device has on one hand a large flexibility in the axial direction which allows the device to bend simultaneously with the vascular or hollow organ even if the bending is very localized because the long branches of the U-shape is easily deformed in the axial direction and, on the other hand, the device is very rigid towards localized radial compression because the U-shaped branches of each row of cells form two circumferential rings having large stiffness in their plane. The flexibility of the device in the axial direction further ensures that a local deformation of the vessel does not cause the device to lengthen in the axial direction as the deformation is absorbed within the pressure affected rows of cells. This causes the device to stay fixed with respect to the surrounding supported wall of the vascular or hollow organ so that traumatization is avoided. Under the action of external compression force the ringshape is essentially uniformly loaded. The axial stiffness of the device may to some extent be adjusted to needs by varying the cross-sectional area of the frame wire. By varying the number of cells in the frame, it becomes possible to select the optimum axial stiffness of the frame, so that the vascular or hollow organ wall is traumatized as little as possible.

In a preferred embodiment adjacent cells in one row are interconnected in a flexible manner at the axially extending portion of the U-shaped wire sections. The flexible interconnection allows large deformations of the initially unloaded cell geometry without large deformations in the wire proper because the wire sections are not rigidly fixed to each other.

When the device is to be introduced the ends of the tubular frame are pulled away from each other and the frame diameter is reduced until the frame can be inserted into a delivery catheter. During lengthening of the frame the major portion of cell deformation occurs in the long branches of the wire sections and it is assumed that the axially extending portion of the U-shaped wire sections is only slightly deformed so that the entire U-shaped wire section is substantially uniformly loaded. Consequently, the diameter of the turbular frame may be drastically reduced during insertion without exceeding the elastic strain limit of the wire material. This makes it possible to use devices according to the invention within a wide range of sizes and to introduce the devices through a small puncture hole in the patient, even if the wire is made of e.g. stainless steel.

Preferably the flexible interconnections are accomplished by winding the axially extending portions around each other, more preferably so that the one wire portion is wound only one turn around the associated wire portion. During deformation of the U-shaped wire sections the windings may move apart and/or open which reduces strain in the wire. The wound wire portions also act as a kind of hinge joint allowing the two U-shaped wire sections in a cell to swivel with respect to each other when the frame is radially loaded. The wound flexible interconnections present a further advantage, namely that as an alternative to axially lengthening of the frame prior to insertion in the catheter the tubular frame may be twisted about its longitudinal axis by turning the two frame ends in opposite directions. This causes the wound interconnections to open and the frame to collaps to a reduced diameter allowing insertion. When the frame after positioning abreast of the site to be supported is pushed out of the catheter it "uncoils" to its initial diameter without any substantial axial shortening of the frame, which leads to an uncomplicated and very precise positioning of the device in the vascular or hollow organ.

In a further embodiment which is preferred due to its simplicity of manufacture the device is characterized in that each U-shaped wire section is composed of two separate wires each of which runs in substantially helical shape through the rows of cells, and that the two wires are wound, preferably on turn, around each other at the axially extending portion where they meet to form the bottom leg of the U-shape.

The device may have wires of a shape memory alloy exhibiting thermally activated shape memory properties, preferably a NiTi-alloy, but more preferably the wires are of a shape memory alloy exhibiting superelastic properties, advantageously a NiTi-alloy. Such a shape memory alloy can be excessively deformed and yet return to its set predetermined shape without loss of stiffness or introduction of permanent deformations in the wire. The shape memory alloy wire frame can be reduced to a diameter of only a few mm during insertion irrespective of its unloaded diameter which e.g. may be as large as 50 mm so that the frame can be introduced into the patient through a single small diameter catheter which only requires a small puncture hole in the patient. The superelastic alloy is preferred in order to avoid thermal control during insertion. When this alloy is deformed it exhibits stress induced martensite.

The above described possibilities of variation of the axial and radial stiffness of the frame allow the latter to fulfil the function of sustaining of the vessel or hollow organ lumen within any range of their standard sizes, for example, from a diameter of 3 mm to a diameter of 50 mm, and be applicable in different anatomical areas of the vessel or hollow organ and even to be introduced along a tortous path. The device may also be used for retention of blood clots as a Cavafilter.

Figure 2:
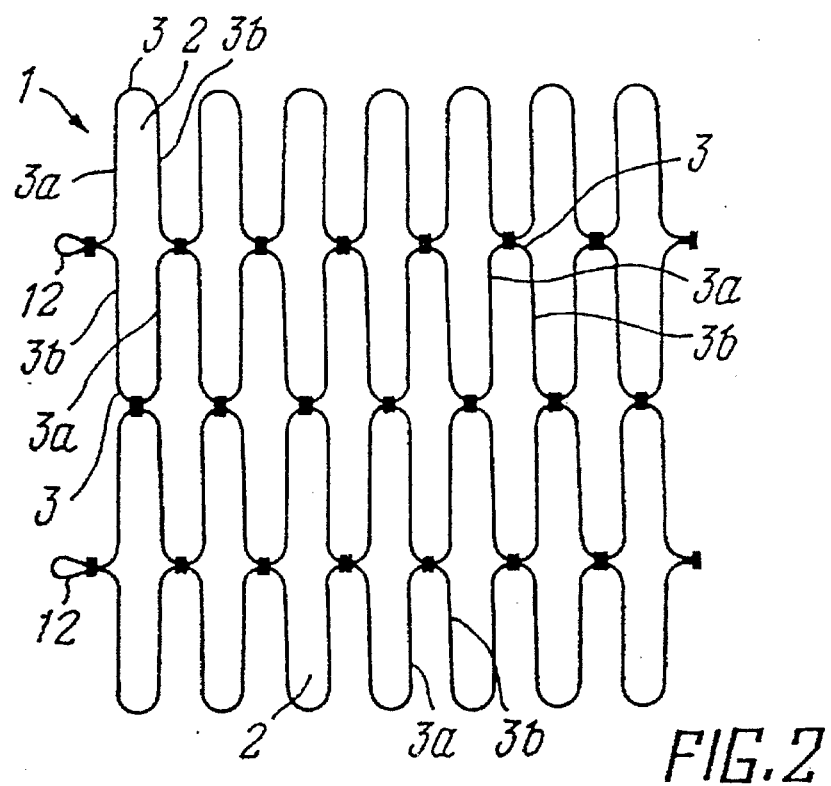
Figure 4:
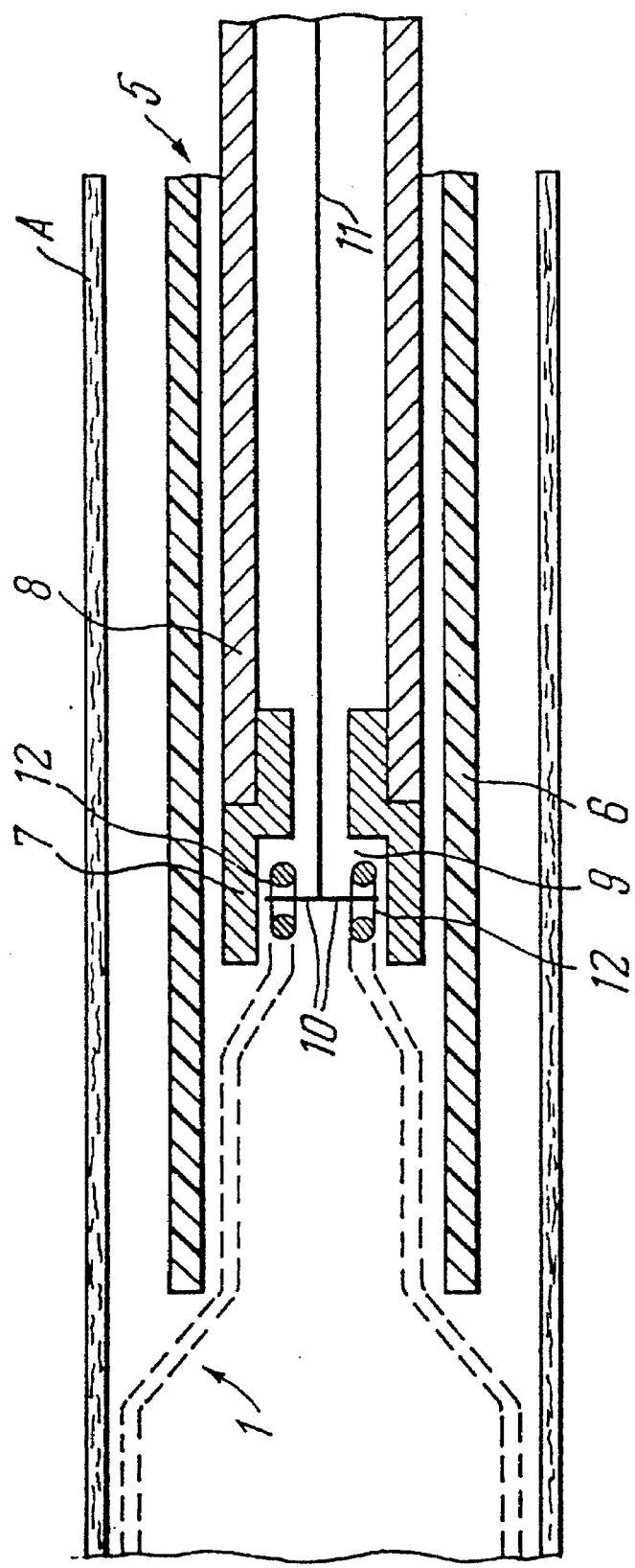
Figure 4A:
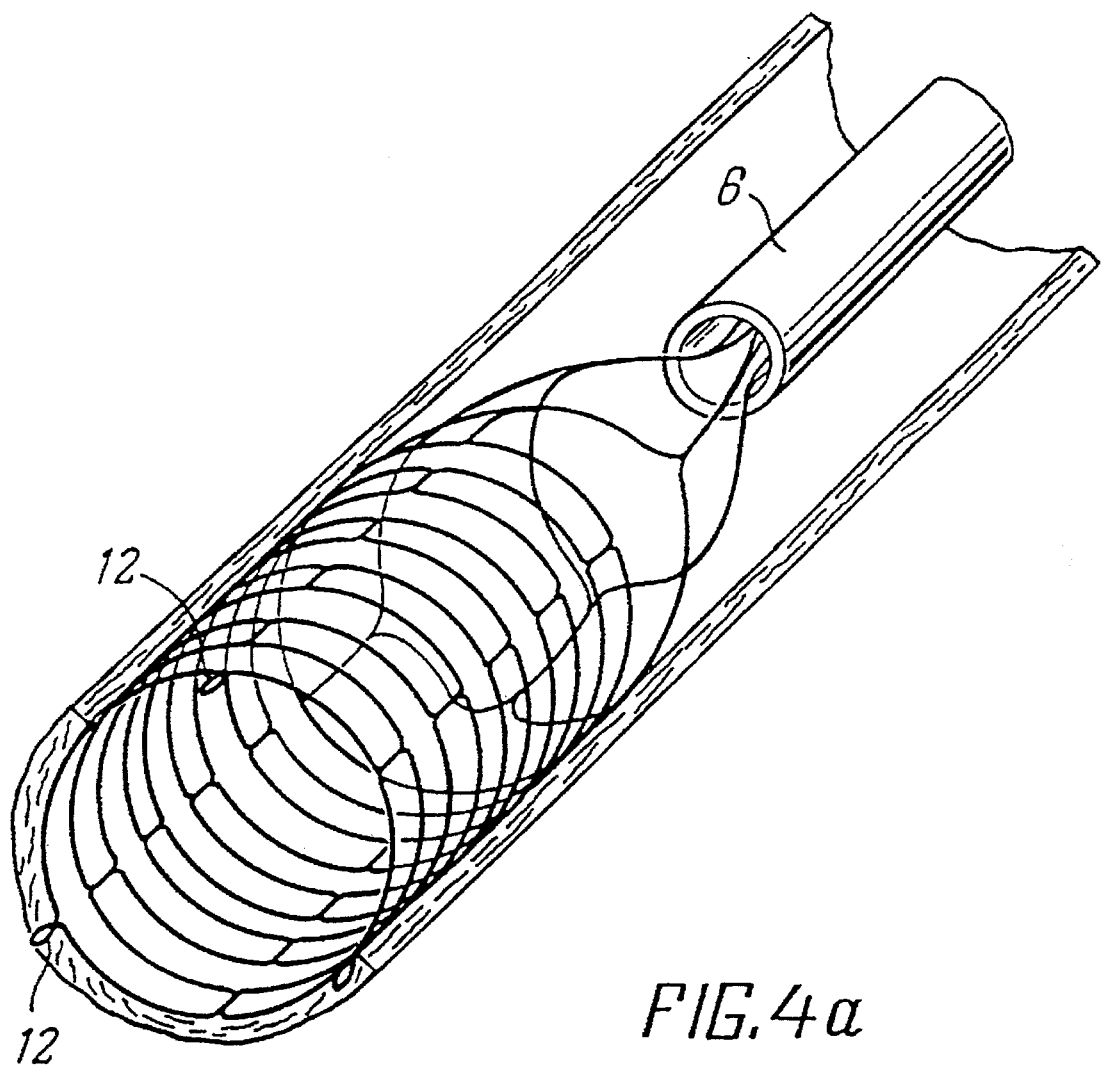
Figure 5:
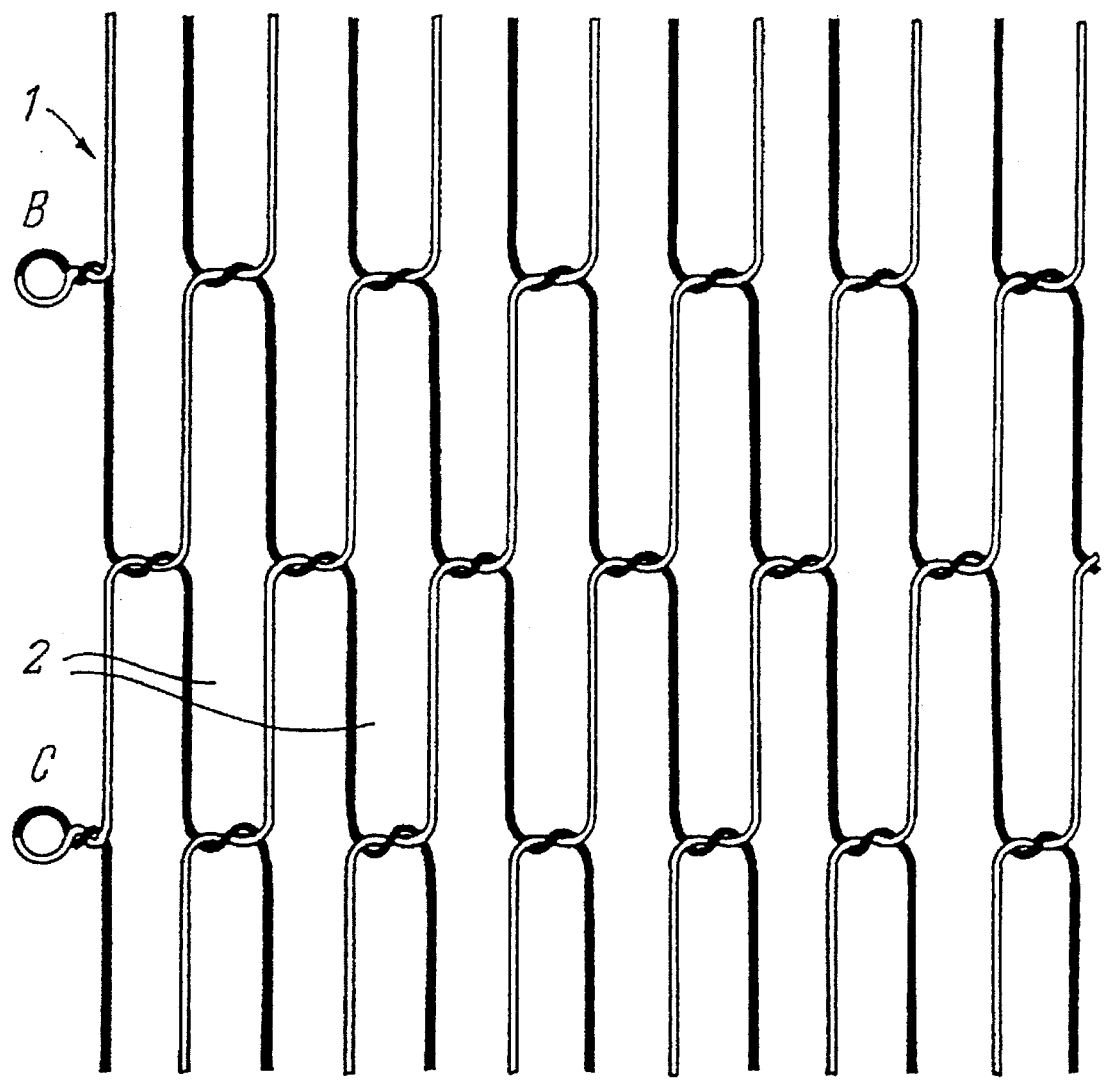

In the following description examples of embodiments of the device according to the invention is described in futher detail with reference to the schematical drawings, in which FIG. 1 shows a perspective view of the device for sustaining a vessel or hollow organ lumen, according to the invention, FIG. 2 shows in a larger scale, a development of the frame surface, FIG. 3 is a section after line III—III in FIG. 1, FIG. 4 and 4a illustrate the delivery device with the frame in longitudinal section and perspective view, respectively, and FIG. 5 shows in development a section of the frame surface in a second embodiment according to the invention, in large scale.

The device for sustaining the lumen, for example of the femoral artery, accomplished in accordance with the invention, has wire frame 1 in the form of a tubular shaped body, for example in the form of a cylindrical body.

The cylindrical surface of frame 1 shown in development in FIG. 2 is formed by a large number of interconnected cells 2 formed by two U-shaped wire sections 3, interconnected by their branches 3a, 3b, and forming approximately an oval, whose larger axis is arranged in the circumferential direction of the body and the smaller axis parallel to its axial direction. Cell 2 of each subsequent row is shifted in the circumferential direction with respect to cell 2 of the present row by ½ of the length of the oval larger axis. Each branch 3a or 3b of the U-shaped wire section 3 belongs to two cells 2 in adjacent rows, except for the first and last rows. In a cross-section of frame 1 in a plane perpendicular to its longitudinal axis and passing through the long branches of the U-shaped wire sections 3 of one row these branches form a closed ringshape 4 which provides the frame with large stiffness in radial direction and ensures that the cell will only to a very limited extent be deformed in the axial direction when it is radially loaded. The wire section 3 may have a circular cross-section as seen in FIG. 3.

The wire can be made of a titanium-nickel alloy having shape memory properties which may either be thermally or stress activated. When the wire is of such an alloy which may be heavily deformed without permanent deformation of the wire, the cells 2 of frame 1 can be interconnected by a rigid joint at the tops of the U-shaped wire sections. Alternatively the U-shaped sections may be flexible interconnected by small rings, e.g. of thread.

The described device is introduced into the vessel A such as the femoral artery as follows. A delivery device 5 comprises a hollow X-ray contrast tube 6, containing a hollow pusher 7 with a rod 8. The pusher has an internal space 9 including two stops 10 in the form of cylindrical radially extending pins rigidly connected with a holder 11 arranged along the longitudinal axis of rod 8. The distance between the extreme points of stops 10 essentially corresponds to the inside diameter of pusher 7. The holder 11 is installed with a possibility of longitudinal displacement.

The frame 1 is secured to the stops 10 of holder 11 by means of lugs 12 inserted over the stops 10. The holder 11 connected to frame 1, is fixed with respect to rod 8. The rod 8 is introduced into X-ray contrast tube 6 simultaneously with the frame 1 being drawn into contrast tube 5 along its longitudinal axis. When entering the contrast tube 6 the sections 3 forming frame 1 acquire a shape close to a straight line and the frame diameter is reduced to a few mm. The forward end of contrast tube 6 is then, through the puncture hole, brought to the affected area of vessel A. Frame 1 may alternatively be brought into tube 6 by rotating holder 11 with respect to the frame end opposite to the end fixed to stops 10 so that the frame 1 is collapsed to small diameter and may be inserted into tube 6.

When the delivery device 5 is in position in the vessel or hollow organ the surgeon, while acting upon frame 1 through rod 8, withdraws the X-ray contrast tube from the frame, so that the wire sections 3 of the device fold out to the original tubular shape.

If the wire is a thermally activated shape memory alloy the blood temperature heats the wire and the device acquires its initial shape. If the wire is superelastic it will simply return to its preset shape when the restraining force from tube 6 is removed.

Recovery of the initial frame shape occurs in succession by forming closed ring-shaped circuits 4 in the plane perpendicular to the device axis. The ring-shaped circuit interacts with the walls of vessel or organ A (FIG. 4a), sustaining its lumen constant and repeating its geometry due to the maximum radial stiffness and optimum axial stiffness of frame 1 (FIG. 1).

The described constructional features of the device make it possible to bring it to the affected area through a minimum puncture hole.

The embodiment shown in FIG. 5 has cells 2 of similar shape as in the above described embodiment, but the cells are interconnected in an alternative manner. Each U-shaped wire section is composed by two different wires which run in substantially helical shape through the rows of cells and the wires and wound one turn around each other at the axially extending wire portion where they meet to form the bottom portion or leg of the U-shape. At the ends of the frame the associated pairs of wires are Joined at points B and C by twinning the wires around each other. The formed loop may be bend into the adjacent outer cell in order not to traumatize the vascular wall. The formed interconnections between the cells are highly flexible and the wires may deform more or less independent of each other.

The device is introduced into the hollow vein, artery or organ A in the same manner as the above described device.

The device preserving the vessel lumen constant and repereting its geometry, has an increased durability because of the movable Joint between the wires.

The accomplished analysis and the obtained positive estimate of the biological compatibility of the described device made it possible to go over to bench tests. The mechanical characteristics of the device were studied on a special model of the arterial system of a human being, and the technical elements of the procedure of its implantation in different areas of the vascular channel were elaborated.

The bench tests have displayed good qualities of the described device and made it possible to set to its use in experimental investigations on animals.

Experiments were conducted on 10 dogs, 3 of them were subjected to an acute experiment, and 7 were subjected to dynamic observations. Implantations were accomplished into the thoracic, abdominal aortas, renal, iliolumbar and femoral arteries. At check X-ray analyses in general terms it was noted that the devices do not shift the places of their initial implantation, the shape of the device conforms to the initial one, no symptoms of thrombosis and stenosis of the vessel were revealed.

We claim:

1. A prosthetic device for sustaining a vessel or hollow organ lumen, comprising:

a flexible, tubular shaped frame (1) of separate first and second helical wires forming flexibly interconnected cells (2), each of the cells including first and second U-shaped sections (3) forming together an approximately elongated oval with a larger axis and a smaller axis, wherein the larger axis of the oval is directed in a circumferential direction of the tubular shaped frame and the smaller axis is directed in a direction parallel to a longitudinal axis of the tubular shaped frame, and wherein in a plane substantially perpendicular to the longitudinal axis of the tubular frame, one branch of each U-shaped wire section in one row together form a closed ring shape.

2. The prosthetic device of claim 1 wherein each of said first and second helical wires is of a superelastic material.

3. The prosthetic device of claim 2 wherein the superelastic material comprises a nickel-titanium alloy.

4. The prosthetic device of claim 1 wherein the flexible, tubular shaped frame is self-expanding.

5. The prosthetic device of claim 1 wherein adjacent cells in neighboring rows are shifted by a predetermined amount of the larger axis of the oval with respect to each other in the direction of the larger axis.

6. The prosthetic device of claim 5 wherein adjacent cells in alternating rows are shifted by the smaller axis of the oval with respect to each other in the direction of the smaller axis.

7. The prosthetic device of claim 1 wherein the flexibly interconnected cells are interconnected by the first and second helical wires wound around each other.

8. The prosthetic device of claim 7 wherein the flexibly interconnected cells are interconnected by the first and second helical wires wound one turn around each other.

9. The prosthetic device of claim 1 wherein the helical wires run through the flexibly interconnected cells and wherein the helical wires are wound one turn around each other where the cells are flexibly interconnected.

10. A prosthetic device for sustaining a vessel or hollow organ lumen, comprising:

a wire frame (1) having a flexible tubular shaped body with rows of interconnected cells (2), the flexible tubular shaped body having a reduced diameter during introduction through a tube or a delivery catheter, each of the cells having two U-shaped wire sections (3) forming an approximately elongated oval with a larger axis and a smaller axis, wherein adjacent cells (2) in neighboring rows are shifted by half of the larger axis of the oval with respect to each other in the direction of the larger axis, wherein the larger axis of the oval is directed in the circumferential direction of the tubular body and the smaller axis parallel to the axial direction thereof so that in a plane perpendicular to the longitudinal axis of the body, one branch of each U-shaped wire section (3) in one row forms together a closed ring shape, and wherein adjacent cells (2) in one row are interconnected in a flexible manner at an axially extending portion of the U-shaped wire sections.

11. A prosthetic device according to claim 10, wherein the flexible interconnections are accomplished by winding the axially extending portions around each other.

12. A prosthetic device according to claim 11, wherein the flexible interconnections are accomplished by winding the one wire portion only one turn around the associated wire portion.

13. A prosthetic device according to claim 11, wherein each U-shaped wire section (3) is composed of two separate wires each of which runs in substantially helical shape through the rows of cells (2) and wherein the two wires are wound around each other at the axially extending portion where the two wires meet to form the bottom leg of the U-shape.

14. A prosthetic device according to claim 13 wherein the two wires are wound one turn around each other at the axially extending portion where the two wires meet to form the bottom leg of the U-shape.

15. A prosthetic device according to claim 10 wherein the wires are of a shape memory alloy exhibiting thermally activated shape memory properties.

16. A prosthetic device according to claim 15 wherein the shape memory alloy comprises a nickel-titanium alloy.

17. A prosthetic device according to claim 15 wherein the wires of the shape memory alloy exhibit superelastic properties.

18. A prosthetic device according to claim 10 wherein the wires are of a superelastic alloy.

19. A prosthetic device according to claim 18 wherein the superelastic alloy comprises a nickel-titanium alloy.

20. A prosthetic device for sustaining a vessel or hollow organ lumen, comprising:

a self-expanding wire frame (1) having a flexible tubular shape and rows of flexibly interconnected cells (2), each of the cells including first and second U-shaped wire sections (3) forming together an approximately elongated oval with a larger axis and a smaller axis, wherein each U-shaped wire section includes two separate wires each of which runs in a substantially helical shape through the rows of cells, wherein the two separate wires are wound one turn around each other at an axially extending portion where the two separate wires meet to form a bottom leg of the U-shape, wherein adjacent cells (2) in neighboring rows are shifted by half of the larger axis of the oval with respect to each other in the direction of the larger axis, wherein the larger axis of the oval is directed in a circumferential direction of the tubular shaped frame and the smaller axis parallel to the longitudinal axis of the tubular shaped frame, wherein in a plane perpendicular to the longitudinal axis of the tubular shaped frame, one branch of each U-shaped wire section (3) in one row forms together a closed ring shape, wherein adjacent cells (2) in one row are interconnected in a flexible manner at the axially extending portion of the U-shaped wire sections, wherein the two separate wires are a nickel-titanium alloy exhibiting superelastic properties.

* * * * *